United States Patent
Trail (10) Patent No.: US 10,261,542 B1
(45) Date of Patent: *Apr. 16, 2019

(54) DISTRIBUTED AUGMENTED REALITY SYSTEM

(71) Applicant: Facebook Technologies, LLC, Menlo Park, CA (US)

(72) Inventor: Nicholas Daniel Trail, Bothell, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/034,148

(22) Filed: Jul. 12, 2018

Related U.S. Application Data (63) Continuation of application No. 15/676,626, filed on Aug. 14, 2017, now Pat. No. 10,061,352.

(51) Int. Cl.

| G06F 1/16 | (2006.01) |
|---|---|
| G02B 27/01 | (2006.01) |
| A61B 5/00 | (2006.01) |
| H04R 1/08 | (2006.01) |
| G02C 3/00 | (2006.01) |
| H02J 50/10 | (2016.01) |
| G06F 3/16 | (2006.01) |
| G06F 3/01 | (2006.01) |

(52) U.S. Cl.
CPC ............ *G06F 1/163* (2013.01); *A61B 5/6822* (2013.01); *A61B 5/6831* (2013.01); *G02B 27/0172* (2013.01); *G02B 27/0176* (2013.01); *G02C 3/006* (2013.01); *G06F 3/013* (2013.01); *G06F 3/017* (2013.01); *G06F 3/167* (2013.01); *H02J 50/10* (2016.02); *H04R 1/08* (2013.01); *G02B 2027/014* (2013.01); *G02B 2027/0138* (2013.01); *G02B 2027/0161* (2013.01)

(58) Field of Classification Search
CPC ....... G06F 1/163; G06F 1/1637; G02B 27/01; G02B 27/017; G02B 27/0176
USPC .................................................... 361/679.03
See application file for complete search history.

(56) References Cited

U.S. PATENT DOCUMENTS

| 5,078,134 A * | 1/1992 | Heilman ............... A61B 5/6831 600/508 |
| 5,285,398 A * | 2/1994 | Janik ....................... G06F 1/163 361/679.03 |
| 5,305,244 A * | 4/1994 | Newman ................ G01R 1/025 704/E15.045 |

(Continued)

*Primary Examiner* — Adrian S Wilson
(74) *Attorney, Agent, or Firm* — Fenwick & West LLP (57) ABSTRACT

A distributed augmented reality system for producing rendered environment includes a neckband formed from a first arm, second arm, and computation compartment. A power source is embedded in the first and/or second arm, while a processor is embedded in the computation compartment of the neckband. The neckband may be capable of producing an AR, VR or MR environment, or any combination thereof. The neckband device may be used with a coupled eyewear device system encompassing a Near-Eye Display (NED) and/or secondary user device, which may also produce an AR, VR or MR environment, or any combination thereof. The neckband device may provide power and computation to the eyewear device, allowing for a reduced form factor AR/VR/MR eyewear device.

20 Claims, 5 Drawing Sheets

(56) References Cited

U.S. PATENT DOCUMENTS

| | | | | |
|---|---|---|---|---|
| 5,416,310 A * | | 5/1995 | Little | G06F 1/163 2/102 |
| 5,774,338 A * | | 6/1998 | Wessling, III | A41D 13/0012 2/94 |
| 5,995,936 A * | | 11/1999 | Brais | G02B 27/017 369/25.01 |
| 6,091,546 A * | | 7/2000 | Spitzer | G06F 19/00 359/618 |
| 6,108,197 A * | | 8/2000 | Janik | G06F 1/163 361/679.03 |
| 6,356,437 B1 * | | 3/2002 | Mitchell | G06F 1/163 342/352 |
| 6,443,347 B1 * | | 9/2002 | Elizalde | A45F 3/14 224/245 |
| 6,727,865 B1 * | | 4/2004 | Yonezawa | G02B 27/017 345/7 |
| 6,734,834 B1 * | | 5/2004 | Baram | A61B 5/1101 345/156 |
| 6,747,611 B1 * | | 6/2004 | Budd | G02B 27/0172 345/7 |
| 6,762,885 B1 * | | 7/2004 | Ogasawara | G02B 27/0176 345/8 |
| 6,798,391 B2 * | | 9/2004 | Peterson, III | G06F 1/163 345/8 |
| 6,956,614 B1 * | | 10/2005 | Quintana | G06F 1/163 348/158 |
| 7,199,934 B2 * | | 4/2007 | Yamasaki | G02B 27/0093 345/7 |
| 7,969,383 B2 * | | 6/2011 | Eberl | G02B 27/017 345/7 |
| 9,779,478 B1 * | | 10/2017 | Wilson | G06T 3/4092 |
| 9,858,672 B2 | | 1/2018 | Trail | |
| 9,972,071 B2 | | 5/2018 | Wilson et al. | |
| 9,976,849 B2 | | 5/2018 | Trail | |
| 10,061,352 B1 * | | 8/2018 | Trail | G06F 1/163 |
| 2003/0068057 A1 * | | 4/2003 | Miller | H04B 1/385 381/334 |
| 2006/0132382 A1 * | | 6/2006 | Jannard | G02C 11/06 345/8 |
| 2008/0169998 A1 * | | 7/2008 | Jacobsen | G02B 27/0172 345/8 |
| 2010/0171680 A1 * | | 7/2010 | Lapidot | G02B 27/017 345/8 |
| 2011/0001699 A1 * | | 1/2011 | Jacobsen | G06F 3/012 345/157 |
| 2012/0204307 A1 * | | 8/2012 | De Mattei | A41D 1/002 2/69 |
| 2012/0293935 A1 * | | 11/2012 | Sherlock | G06F 1/163 361/679.03 |
| 2013/0208234 A1 | | 8/2013 | Lewis | |
| 2015/0241959 A1 * | | 8/2015 | Abovitz | G06K 9/00671 345/633 |
| 2017/0123526 A1 * | | 5/2017 | Trail | G06F 3/041 |
| 2017/0134717 A1 * | | 5/2017 | Trail | G06T 19/006 |
| 2017/0139211 A1 * | | 5/2017 | Trail | G02B 27/0172 |
| 2017/0180713 A1 * | | 6/2017 | Trail | G06F 3/011 |
| 2017/0192499 A1 * | | 7/2017 | Trail | G06F 3/013 |
| 2017/0195653 A1 * | | 7/2017 | Trail | H04N 13/366 |
| 2017/0206660 A1 * | | 7/2017 | Trail | G06T 7/521 |
| 2017/0235380 A1 * | | 8/2017 | Sendai | G06F 3/0487 345/173 |
| 2017/0262054 A1 * | | 9/2017 | Lanman | G06F 3/013 |
| 2017/0293146 A1 * | | 10/2017 | Nicholls | G02B 27/0172 |
| 2018/0048880 A1 * | | 2/2018 | Trail | H04N 5/2256 |
| 2018/0058844 A1 | | 3/2018 | Trail | |
| 2018/0063390 A1 * | | 3/2018 | Trail | H04N 5/2256 |
| 2018/0063508 A1 * | | 3/2018 | Trail | H04N 13/243 |
| 2018/0096458 A1 | | 4/2018 | Wilson et al. | |
| 2018/0096471 A1 * | | 4/2018 | Wilson | G06T 5/50 |

* cited by examiner

DISTRIBUTED AUGMENTED REALITY SYSTEM

CROSS REFERENCE TO RELATED APPLICATIONS

This application is a continuation of U.S. application Ser. No. 15/676,626, filed Aug. 14, 2017, which is incorporated by reference in its entirety.

BACKGROUND

The present disclosure generally relates to augmented reality (AR) systems, and specifically relates to a distributed AR system.

Augmented reality systems and environments allow a user to directly or indirectly view a real world environment augmented by generated sensory input, which may be superimposed on the real world environment. Sensory input can be any form of media, such as sound, video, graphics, etc. Because AR systems allow for users to continue to engage with their real world environments in addition to a generated one, users may have less tolerance for large AR devices, as opposed to a virtual reality (VR) system in which the user is typically immersed in a fully generated environment. Thus AR devices tend to have smaller form factors than typical VR devices.

However, the reduced form factor of AR devices produces challenges for providing sufficient power and computation, and limits the capacity for adding additional features that may enhance the user's AR experience. Often AR devices are very heavy, or sacrifice battery and computation power to minimize weight and heat generation, resulting in devices with short battery life and reduced AR capabilities. Additionally, because most AR devices are Head Mounted Displays (HMDs), the weight of the AR device is limited by the weight carrying capacity of a user's soft-tissue and neck muscles. In addition, the heat generated by both the battery and processor may be uncomfortable to a user, especially since the reduced form factor has limited surface area over which to diffuse the generated heat.

SUMMARY

A distributed system that is configured to distribute processing and functionality among a plurality of devices that together provide a virtual reality (VR), an augmented reality (AR), and/or mixed reality (MR) environment. The system includes a neckband that handles processing offloaded to it from other devices in the system. The neckband includes a first arm, a second arm, a power source, and a computation capability. The power source is embedded in at least one of the first arm and the second arm, and is configured to power an eyewear device that includes at least one sensor. The computation compartment is connected to the first arm and the second arm, the computation compartment, the first arm and the second arm are configured to conform to a user's neck. A processor is embedded in the computation compartment, and the processor configured to compute at least one value from the at least one sensor.

The neckband device is communicatively coupled with the eyewear device. For example, the neckband may be communicatively coupled to an eyewear device and/or other devices. Other devices may include, e.g., a mobile phone. The other devices in the system may provide certain functions (e.g., hand tracking, depth mapping, processing, storage, etc.) to the system. Additionally, in some embodiments, the neckband may also provide power to one or more devices of the system. Offloading power (e.g., battery location), computation, and additional features from devices in the system to the neckband device reduces weight, heat profile and form factor of those devices while still retaining full AR, VR, and/or MR functionality.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION OF THE DRAWINGS

AR and/or mixed reality (MR) devices allow a user to directly or indirectly view a real world environment augmented by generated sensory input, such as sound, video, graphics, etc. The generated sensory input may be superimposed on the real world environment, allowing the user to interact with both simultaneously. In order to allow the user to continue to view his or her real world environment while also perceiving the augmented environment, AR devices ideally provide a minimally invasive interface for the user, which can be easily removed and put on. One category of AR, virtual reality (VR), and/or MR device designs includes a near-eye display (NED) with optical elements that provide the user with generated visual input such as graphics or video. A NED may be imbedded in an eyewear device in the form of eyeglasses, which rest on the bridge of a user's nose. However, when the form factor of the eyewear device is reduced down to the size of a pair of glasses, spatial constraints may limit the battery and computation power of the device. Spatial constraints may also prevent additional features from being incorporated into the device, such as audio, additional cameras, or add-on features that enhance the AR environment, VR environment, and/or MR environment. Additionally, to make the eyewear device comfortable for the user to wear, the weight of the device is limited by what a user would tolerate in a pair of eyeglasses or sunglasses, and also by the carrying capacity of a user's soft tissue and neck muscles. Furthermore, the heat generated by a battery or processor may make the small form factor of the eyewear device uncomfortable, as there is limited surface area over which to disperse generated heat. Often these spatial, weight, and heat constraints result in eyewear devices with short battery life, reduced computation power, and limited feature sets.

One way to allow eyewear devices to achieve the form factor of a pair of glasses, while still providing sufficient battery and computation power and allowing for expanded capabilities (e.g., AR, VR, and/or MR) is to use a paired neckband device. The power, computation and additional features may then be moved from the eyewear device to the neckband device, thus reducing the weight, heat profile, and form factor of the eyewear device overall, while still retaining full AR, VR, and/or MR functionality. The neckband device allows components that would otherwise be included on the eyewear device to be heavier, since users may tolerate a heavier weight load on their shoulders than they would otherwise tolerate on their heads, due to a combination of soft-tissue and gravity loading limits. The neckband device also has a larger surface area over which to diffuse and disperse generated heat to the ambient environment. Thus the neckband device allows for greater battery and computation capacity than might otherwise have been possible simply on a stand-alone eyewear device. The neckband also allows for additional features that supplement the AR, VR and/or MR experience of the user, besides simply the optical elements and sensors within the eyewear device. The neckband device may also be capable of use independently of the eyewear device, and can produce its own AR, VR and/or MR experience for the user, which may be audio or visual based AR, VR and/or MR. Since a neckband device may be less invasive to a user than the eyewear device, the user may tolerate wearing the neckband device for greater lengths of time than the eyewear device, allowing the AR, VR and/or MR environment to be incorporated more fully into a user's day to day activities.

The neckband may also be coupled with a secondary user device, which may be any common user device such as a mobile device, watch, bracelet, or any other wearable device. The neckband integrates with the secondary user device to create an extended AR, VR and/or MR environment for the user besides simply the eyewear device and neckband. The secondary user device may track a user's movement, providing further information about the user's interactions with the AR, VR and/or MR environment. The secondary user device allows for further power, processing and heat distribution to be added to the AR, VR and/or MR system.

Figure 1:
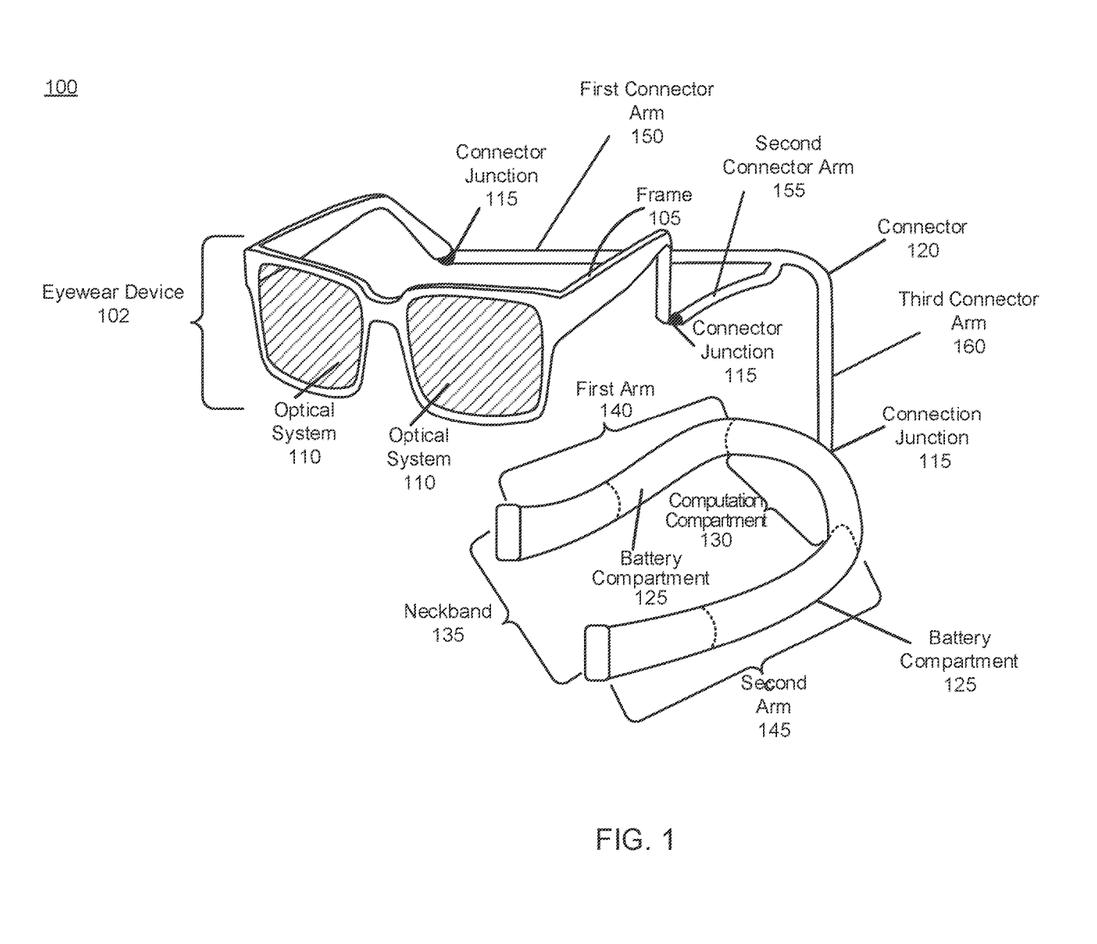
FIG. 1 is a diagram of a distributed system, in accordance with an embodiment.

FIG. 1 is a diagram of a distributed system 100, in accordance with an embodiment. The distributed system 100 includes an eyewear device 102 and a neckband 135. In alternate embodiments, the distributed system 100 may include additional components (e.g., a mobile device as discussed in detail below with regard to FIGS. 6 and 7).

The eyewear device 102 provides content to a user of the distributed system 100. The eyewear device 102 includes two optical systems 110. The eyewear device 102 may also include a variety of sensors, such as one or more passive sensors, one or more active sensors, one or more audio devices, an eye tracker system, an inertial measurement unit (not shown), or some combination thereof. As shown in FIG. 1, the eyewear device 102 and optical systems 110 are formed in the shape of eyeglasses, with the two optical systems 110 acting as eyeglass "lenses" and a frame 105. The frame 105 is attached to a connector 120 by connector junctions 115. The connector junctions 115 also attach connector 120 to the neckband 135.

Optical systems 110 present visual media to a user. Each of the optical systems 110 may include a display assembly. In some embodiments, when the eyewear device 102 is configured as an AR eyewear device, the display assembly also allows and/or directs light from a local area surrounding the eyewear device 102 to an eyebox (i.e., a region in space that would be occupied by a user's eye). The optical systems 110 may include corrective lenses, which may be customizable for a user's eyeglasses prescription. The optical systems 110 may be bifocal corrective lenses. The optical systems 110 may be trifocal corrective lenses.

The display assembly may be composed of one or more materials (e.g., plastic, glass, etc.) with one or more refractive indices that effectively minimize the weight and widen a field of view of the eyewear device 102 visual system. In alternate configurations, the eyewear device 102 includes one or more elements between the display assembly and the eye. The elements may act to, e.g., correct aberrations in image light emitted from the display assembly, correct aberrations for any light source due to the user's visual prescription needs, magnify image light, perform some other optical adjustment of image light emitted from the display assembly, or some combination thereof. An element may include an aperture, a Fresnel lens, a convex lens, a concave lens, a liquid crystal lens, a liquid or other deformable surface lens, a diffractive element, a waveguide, a filter, a polarizer, a diffuser, a fiber taper, one or more reflective surfaces, a polarizing reflective surface, a birefringent element, or any other suitable optical element that affects image light emitted from the display assembly.

Examples of media presented by the eyewear device 102 include one or more images, text, video, audio, or some combination thereof. The eyewear device 102 can be configured to operate, in the visual domain, as a VR NED, an AR NED, a mixed reality (MR) NED, or some combination thereof. For example, in some embodiments, the eyewear device 102 may augment views of a physical, real-world environment with computer-generated elements (e.g., images, video, sound, etc.). The eyewear device 102 may include a speaker or any other means of conveying audio to a user, such as bone conduction, cartilage conduction, etc.

In other embodiments, the eyewear device 102 does not present media or information to a user. For example, the eyewear device 102 may be used in conjunction with a separate display, such as a coupled mobile device or laptop (not shown). In other embodiments, the eyewear device 102 may be used for various research purposes, training applications, biometrics applications (e.g., fatigue or stress detection), automotive applications, communications systems for the disabled, or any other application in which eye tracking or other sensing functions can be used.

The eyewear device 102 may include embedded sensors (not shown) such as 1-dimensional (1D), 2-dimensional (2D) imagers, or scanners for localization and stabilization of the eyewear device 102, as well as sensors for understanding the user's intent and attention through time. The sensors located on the eyewear device 102 may be used for Simultaneous Localization and Mapping (SLAM) calculations, which may be carried out in whole or in part by the processor embedded in the computation compartment 130 and/or a processor located in a coupled mobile device, as described in further detail with reference to FIG. 6. Embedded sensors located on the eyewear device 102 may have associated processing and computation capabilities.

In some embodiments, the eyewear device 102 further includes an eye tracking system (not shown) for tracking a position of one or both eyes of a user. Note that information about the position of the eye also includes information about an orientation of the eye, i.e., information about user's eye-gaze. Based on the determined and tracked position and orientation of the eye, the eyewear device 102 adjusts image light emitted from one or both of the display assemblies. In some embodiments, the eyewear device 102 adjusts focus of the image light through the optical systems 110 and ensures that the image light is in focus at the determined angle of eye-gaze in order to mitigate the vergence-accommodation conflict (VAC). Additionally or alternatively, the eyewear device 102 adjusts resolution of the image light by performing foveated rendering of the image light, based on the position of the eye. Additionally or alternatively, the eyewear device 102 uses the information on a gaze position and orientation to provide contextual awareness for the user's attention, whether on real or virtual content. The eye tracker generally includes an illumination source and an imaging device (camera). In some embodiments, components of the eye tracker are integrated into the display assembly. In alternate embodiments, components of the eye tracker are integrated into the frame 105. Additional details regarding incorporation of eye tracking system and eyewear devices may be found at, e.g., U.S. patent application Ser. No. 15/644,203, which is hereby incorporated by reference in its entirety.

Computation for the eye-tracking system may be carried out by the processor located in the computation compartment 130 and/or a coupled mobile device, as described in further detail with reference to FIG. 6. The eyewear device 102 may include an IMU sensor (not shown) to determine the position of the eyewear device relative to a user's environment, as well as detect user movement. The IMU sensor may also determine the relative spatial relationship between the eyewear device 102 and the neckband 135, which may provide information about the position of the user's head relative to the position of the user's body. Here the neckband 135 may also include an IMU sensor (not shown) to facilitate alignment and orientation of the neckband 135 relative to the eyewear device 102. The IMU sensor on the neckband 135 may determine the orientation of the neckband 135 when it operates independently of the eyewear device 102. The eyewear device 102 may also include a depth camera assembly (not shown), which may be a Time-of-Flight (TOF) camera, a Structured Light (SL) camera, a passive and/or active stereo system, and may include an infrared (IR) light source and detection camera. The eyewear device 102 may include a variety of passive sensors, such as a red green and blue (RGB) color camera, passive locator sensors, etc. The eyewear device 102 may include a variety of active sensors, such as structured light sensors, active locators, etc. The number of active sensors may be minimized to reduce overall weight, power consumption and heat generation on the eyewear device 102. Active and passive sensors, as well as camera systems may be placed anywhere on the eyewear device 102.

The neckband 135 is a wearable device that performs processing intensive operations offloaded to it from other devices (e.g., the eyewear device 102, a mobile device, etc.). The neckband 135 is composed of a first arm 140 and a second arm 145. As shown, battery compartment 125 is embedded in both the first arm 140 and the second arm 145. As shown, a computation compartment 130 is connected to both the first arm 140 and the second arm 145. The computation compartment 130 is also attached to the connector 120 by connector junction 115. The connector 120 attaches the computation compartment 130 to the frame 105 of the eyewear device 102 at connector junctions 115.

Any of the above components may be located in any other part of the neckband 135. There may be any number of battery compartments 125 distributed across the neckband 135. There may be any number of computation compartments 130 distributed across the neckband 135. The battery compartment 125 and computation compartment 130 are preferably located such that weight is distributed evenly across the neckband 135, from left-to-right across the device symmetrical axis. Battery compartments may be located symmetrically across the device symmetrical axis, or may be asymmetrically distributed to balance out the weight of other sensors or compartments. For example, the battery compartments 125 may be located on the first arm 140 to balance out a computation compartment located on the second arm 145.

The neckband 135, composed of the first arm 140, the second arm 145 and the computation compartment 130, is formed in a "U" shape that conforms to the user's neck. The neckband 135 is worn around a user's neck, while the eyewear device 102 is worn on the user's head (not shown) as described in further detail with respect to FIG. 2. The first arm 140 and second arm 145 of the neckband 135 may each rest on the top of a user's shoulders close to his or her neck such that the weight of the first arm 140 and second arm 145 are carried by the user's neck base and shoulders. The computation compartment 130 may sit on the back of a user's neck. The connector 120 is long enough to allow the eyewear device 102 to be worn on a user's head while the neckband 135 rests around the user's neck. The connector 120 may be adjustable, allowing each user to customize the length of connector 120.

The power source in the battery compartment 125 may be in one or more sub-assemblies (with two as shown) where the unit embedded in the first arm 140 and/or the battery compartment 125 in the second arm 145 powers the eyewear device 102. Each battery compartment 125 houses a power source (e.g., batteries) which may be re-chargeable. The power source in the battery compartment 125 may be lithium ion batteries, lithium-polymer battery, primary lithium batteries, alkaline batteries, or any other form of power storage. If more than one battery sub-assembly is utilized, the battery compartment 125 of the first arm 140 may have a different battery or power capacity than the battery in the battery compartment 125 of the second arm 145. The computation compartment 130 may have its own power source (not shown) and/or may be powered by a power source in the battery compartments 125. Locating the battery compartments 125 on the neckband 135 distributes the weight and heat generated by the battery compartment 125 from the eyewear device 102 to the neckband, which may better diffuse and disperse heat, and also utilizes the carrying capacity of a user's neck base and shoulders. Locating the battery compartments 125, computation compartment 130 and any number of other sensors on the neckband device 135 may also better regulate the heat exposure of each of these elements, as positioning them next to a user's neck may protect them from solar and environmental heat sources The computation compartment 130 houses a processor (not shown), which processes information generated by any of the sensors or camera systems on the glasses 102 and/or the neckband 135. Information generated by the eyewear device 102 and the neckband 135 may also be processed by a mobile device, such as the mobile device described in further detail with reference to FIG. 6. The processor in the computation compartment 130 may process information generated by both the eyewear device 102 and the neckband 135. The connector 120 conveys information between the eyewear device 102 and the neckband 135, and between the eyewear device 102 and the processor in the computation compartment 130. In some examples, the first arm 140, and second arm 145 may also each have an embedded processor (not shown). In these examples, the connector 120 conveys information between the eyewear device 102 and the processor in each of the first arm 140, the second arm 145 and the computation compartment 130. The information may be in the form of optical data, electrical data, or any other transmittable data form. Moving the processing of information generated by the eyewear device 102 to the neckband 135 reduces the weight and heat generation of the eyewear device 102, making it more comfortable to the user.

The processor embedded in the computation compartment 130 may compute all inertial and spatial calculations from the IMU sensor located on the eyewear device 102. The processor embedded in the computation compartment 130 may compute all calculations from the active sensors, passive sensors, and camera systems located on the eyewear device 102. The processor embedded in the computation compartment 130 may perform all computations from information provided by any sensor located on the eyewear device 102. The processor embedded in the computation compartment 130 may perform all computation from information provided by any sensor located on the eyewear device 102 in conjunction with a processor located on a coupled external device, such as a mobile device as described in further detail with reference to FIG. 6.

The neckband 135 may include a multifunction compartment, as described in further detail with reference to FIG. 3. The multifunction compartment may be a customizable compartment in which additional feature units may be inserted and removed by a user. Additional features may be selected and customized by the user upon purchase of the neckband 135. Examples of units that may be included in a multifunction compartment are: a memory unit, a processing unit, a microphone array, a projector, a camera, etc.

The computation compartment 130 and battery compartment 125 may be segments of the neckband 135 as shown in FIG. 1. However, computation compartments 130 and battery compartments 125 may also be any sub-structures of neckband 135, such as compartments embedded within neckband 135, compartments coupled to sensors embedded in neckband 135, compartments coupled to a multifunction compartment (such as multifunction compartments 330a and/or 330b as shown in FIG. 3), and may be located anywhere on neckband 135.

The connector 120 is formed from a first connector arm 150 that is latched near the end tip of the eyewear device 102 at connector junction 115. A second connector arm 155 is latched near a second end tip of the eyewear device 102 at connector junction 115, and forms a "Y" shape with the first connector arm 150 and second connector arm 155. A third connector arm 160 is shown latched to the neckband 135 computation compartment 130 at connector junction 115. The third connector arm 160 may also be latched at the side of the neckband 135, such as along the first arm 140 or second arm 145. The first connector arm 150 and the second connector arm 155 may be the same length so that the eyewear device 102 sits symmetrically on a user's head. The connector 120 conveys both information and power from the neckband 135 to the eyewear device 102.

In some examples, the connector 120 conveys information from the eyewear device 102 to the neckband 135. Sensors located on the eyewear device 102 may provide the processor embedded in the computation compartment 130 with sensing data, which may be processed by the processor in the computation compartment 130. The computation compartment 130 may convey the results of its computation to the eyewear device 102. For example, if the result of the processor in the computation compartment 130 is a rendered result to be displayed to a user, the computation compartment sends the information through the connector 120 to be displayed on the optical elements 110. In some examples, there may be multiple connectors 120. For example, one connector 120 may convey power, while another connector 120 may convey information.

In some examples, the connector 120 provides power through magnetic induction at the connector junctions 115. In this example, the connector junctions 115 may be retention magnets. The connector 120 may also provide power from the neckband 135 to the eyewear device 102 through any conventional power coupling technique. The connector 120 is flexible to allow for independent movement of the eyewear device 102 relative to the neckband 135. The connector 120 may be retractable, or otherwise adjustable to provide the correct length between the near-eye-display and the neckband 135 for each user, since the distance between a user's head and neck may vary.

In some examples, the eyewear device 102 is wirelessly coupled with the neckband 135. In these examples, the processor embedded in the computation compartment 130 receives information from the eyewear device 102 and the sensors and camera assemblies located on the eyewear device 102 through the wireless signal connection, and may transmit information back to the eyewear device 102 through the wireless signal connection. The wireless connection between the eyewear device 102 and the neckband 135 may be through a wireless gateway or directional antenna, located in the first arm 140 and/or second arm 145 and/or on the eyewear device 102. The wireless connection between the eyewear device 102 and the neckband 135 may be a WiFi connection, a Bluetooth connection, or any other wireless connection capable of transmitting and receiving information. The wireless gateway may also connect the eyewear device 102 and/or the neckband 135 to a mobile device, as described in further detail with reference to FIG. 6.

In some examples in which the eyewear device 102 is wirelessly coupled with the neckband 135, the connector 120 may only transmit power between the neckband 135 and the eyewear device 102. Information between the eyewear device 102 and neckband 135 would thus be transmitted wirelessly. In these examples, the connector 120 may be thinner. In some examples in which the eyewear device 102 is wirelessly coupled with the neckband 135, power may be transmitted between the eyewear device 102 and the neckband 135 via wireless power induction. In some examples, there may be a separate battery or power source located in the eyewear device 102. In some examples in which the eyewear device 102 is wirelessly coupled with the neckband 135, the addition of a connector 120 may be optional.

The eyewear device 102 and neckband 135 architecture thus allows the user's AR, VR and/or MR experience to be through a small form factor eyewear device, while still maintaining the processing and battery power necessary to provide a full AR, VR and/or MR experience. The neckband 135 also allows for additional features to be incorporated that would not otherwise have fit onto the eyewear device 102. In some embodiments, the eyewear device 102 may weigh less than 60 grams (e.g., 50 grams). In some embodiments, the eyewear device 102 may weigh less than 60 grams.

Figures 2, 3:
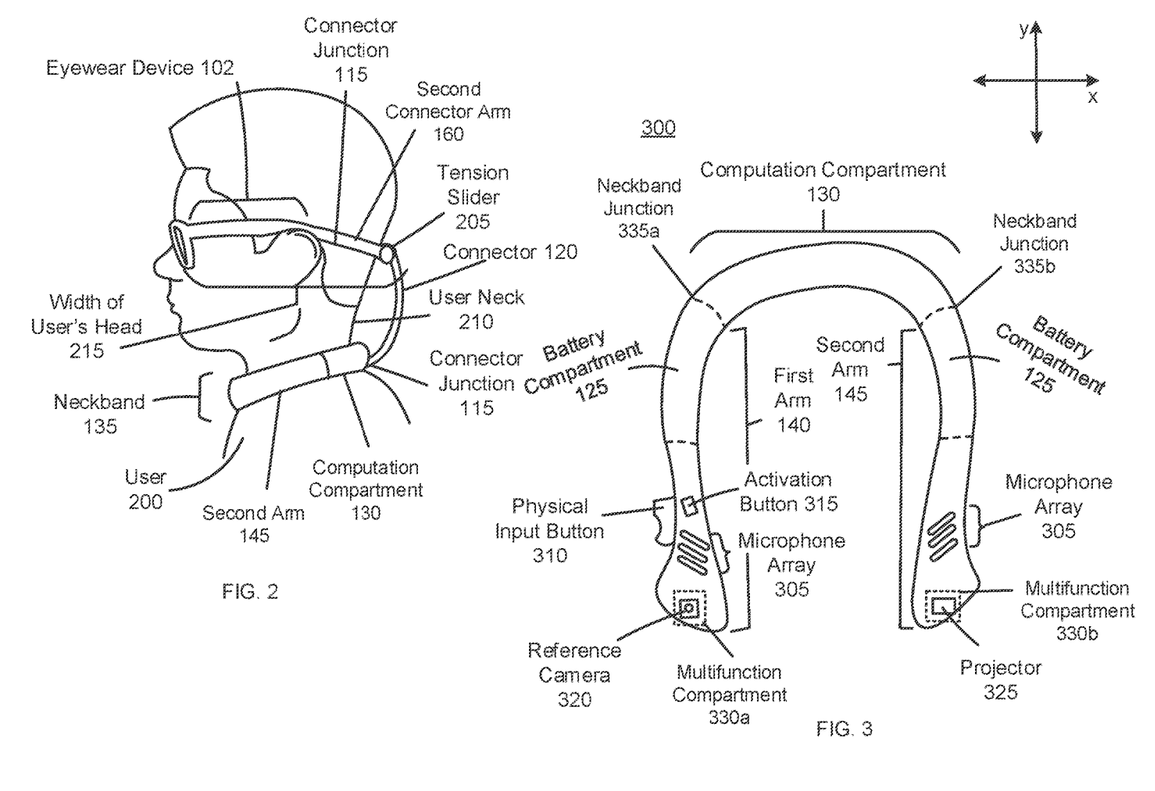
FIG. 2 is a side view of a user wearing the distributed system, in accordance with an embodiment.
FIG. 3 is an overhead view of a neckband, in accordance with an embodiment.

FIG. 2 is a side view of a user wearing the distributed system 100, in accordance with an embodiment. The user 200 wears the eyewear device 102 on his or her head like a pair of eyeglasses. The neckband 135 is shown around the user neck 210, such that the computation compartment 130 is on the back of the user neck 210 and the second arm 145 rests on the side of the user neck 210. Thus the weight of the neckband 135 is distributed to the user's shoulders, and the neckband 135 is conformed to the shape of the user neck 210.

The connector 120 connects the eyewear device 102 to the neckband 135. As described in further detail with respect to FIG. 1, the connector 120 provides power from the neckband 135 to the eyewear device 102, and also conveys information between the eyewear device 102 and the neckband 135. As shown, the connector 120 include a tension slider 205. In some embodiments, the connector 120 may not include a tension slider 205. The tension slider 205 secures the eyewear device 102 to the head of the user 200 by compressing the first connector arm 150 as shown in FIG. 1 to the second connector arm 155. The position of the tension slider can be adjusted to a specific distance between the eyewear device 102 and the neckband 135 such that the width of the user head 215 is approximately the same as the lateral distance from the front of the eyewear device 102 to the position of the tension slider 205, as shown in FIG. 2. In some examples, the tension slider 205 may be secured at a position along the lengths of the first connector arm 150 and the second connector arm 155 through friction between the tension slider 205 and the first connector arm 150 and second connector arm 155. In some examples, the tension slider 205 may be secured by a latching mechanism, such as a clip or fastener that secures the second connector arm 155.

The tension slider 205 may be a single element, or formed from multiple connected elements. In some examples, the tension slider 205 has a single interior cavity through which the first arm 140 and second arm 145 both pass through. In some examples, the tension slider 205 has two interior cavities. The first arm 140 passes through one interior cavity, while the second arm 145 passes through the second interior cavity. The interior cavity through which the first arm 140 and second arm 145 pass may be lined with a material that increases the friction between the interior cavity and the first arm 140 and second arm 145. The interior cavity may be textured to increase friction. The tension slider is lightweight and flexible to provide comfort to the user as it rests against the back of the user's head. The tension slider may be formed from neoprene, an acrylic plastic, rubber, or any other suitable lightweight and flexible material.

The tension slider 205 may allow the user 200 to wear the eyewear device 102 during activities requiring movement of the user 200, such as sporting activities, interactive games, etc. Securing the eyewear device 102 to the head of user 200 may improve the accuracy of inertial calculations estimating the position of the eyewear device 102, as the tension slider and connector 120 may reduce excess movement of the eyewear device 102 on the head of user 200. Thus the tension slider 205 and connector 120 help to more directly couple movement of the eyewear device 102 to actual movements of the user 200 and the head of user 200.

The connector 120 is thus able to provide both power and information coupling between the eyewear device 102 and the neckband 135, while also providing additional securing and stabilization functions.

FIG. 3 is an overhead view of a neckband 300, in accordance with an embodiment. The neckband 300 is formed from a first arm 140, computation compartment 130, and second arm 145. Neckband 300 may be the same neckband 135 as shown in FIGS. 1-2 and 4-7. As shown in FIG. 3, the first arm 140, computation compartment 130, and second arm 145 form a "U" shape that is conformed to the shape of a user's neck.

The neckband 300 may include one or more multifunction compartments (e.g., 330*a*, 330*b*) that interface with function units. A multifunction compartment is a location on the neckband that can receive a functional unit and couple the functional unit to the neckband 300. A functional unit is a sub-system that interfaces with multifunction compartments to provide one or more functions to the neckband 300. Functional units may include, e.g., a reference camera 320, projector 325, a memory unit (not shown), a processing unit (not shown), a microphone array (not shown), a camera, an audio ear-piece, a connector port (such as USB interface), any other sub-system that interfaces with a multifunction compartment to provide a function to the neckband 300, or some combination thereof. A connector port may serve as a power recharging port. As shown in FIG. 3, the neckband 300 contains multifunction compartment 330*a* located on the first arm 140, and multifunction compartment 330*b* located on the second arm 145. As shown in FIG. 3, multifunction compartment 330*a* includes a reference camera 320, while multifunction compartment 330*b* includes a projector 325. Multifunction compartments 330*a* and 330*b* may be located at the end of the first arm 140 and the end of the second arm 145 to be close to a user's mouth for recording the user's voice, if the multifunction compartments 330*a* and 330*b* include a microphone. Multifunction compartments 330*a* and 330*b* may also be located anywhere along the neckband 300.

As shown in FIG. 3, the first arm 140 contains a physical input button 310, an activation button 315, a microphone array 305, and a reference camera 320. As shown in FIG. 3, the second arm 145 contains a microphone array 305 and a projector 325. The neckband 300 may include a memory unit (not shown), a processing unit (not shown), microphone array 305, projector 325, reference camera 320, sensor (not shown) and/or any other unit capable of detecting, recording, or displaying information about the user or the user's environment, or conveying information to and/or from an eyewear device 102 and a mobile device.

The reference camera 320 may provide a near-eye-display or any other device coupled to the neckband 300 with an image of the user interacting with his or her environment. For example, a user may point to an object in the AR or real world environment to request further information about the object. The reference camera records an image of the user pointing to the object, and provides this to the neckband and/or a device coupled to the neckband, such as the near-eye-display shown in FIGS. 1-2 and 4-7 and/or a mobile device as shown in FIG. 6. The coupled device or neckband may then provide the user with the requested information about the object the user indicated. In another example, the reference camera 320 may provide visual information about a user manipulating or interacting with a virtual object that the user perceives in the AR environment. In another example, the reference camera 320 may detect a user's gestures and convert them into commands or use them to adjust controls on the AR, VR and/or MR environment, such as sound volume, on/off, etc.

The physical input button 310 is used for controlling and interfacing with an external device or generated AR, VR and/or MR environment. The physical input button 310 may be a rocker button, a wheel button, or any other input control that may not require a user to directly view the button in order to understand how to input a user choice. In some examples, the physical input button 310 may be used as an I/O button to control volume of a speaker, brightness of the visual media displayed by the neckband 300 itself and/or a coupled AR, VR and/or MR device (such as the eyewear device described in FIGS. 1-2 and 4-7), or to scroll through a menu shown to the user by the neckband 300 and/or a coupled AR, VR and/or MR device. In some examples, the physical input button 310 may be used to control the volume of a speaker, brightness and/or scroll through a menu of a coupled external device with a screen, such as a coupled mobile device, tablet or laptop (not shown). The physical input button 310 is located on the neckband 300 such that it is easily accessible to the user. The physical input button 310 may be in the multifunction compartment 330a located on the first arm 140, as shown in FIG. 3, in the multifunction compartment 330b located on the second arm 145, or anywhere else on the neckband 300 that is convenient for the user to access.

The activation button 315 may be used to turn on or off an AR, VR and/or MR display or any function provided by the neckband 300 and/or a coupled device. In some examples, the activation button 315 initiates an AR, VR and/or MR environment being shown to a user. In some examples, the activation button 315 initiates voice activation of the neckband 300. In some examples, the activation button 315 may select an option in an external menu visible to the user. As shown in FIG. 3, the activation button 315 is one of the multifunction modules located in the multifunction compartment 330a in first arm 140. The activation button 315 may be one of the multifunction modules located in the multifunction compartment 330b of the second arm 145, or anywhere else on the neckband 300 that is convenient for the user to access. The activation button may convey information to the processor in the computation compartment 130 and/or to a coupled AR, VR and/or MR device (such as the eyewear device described in FIGS. 1-2 and 4-7 or a mobile device as described in FIG. 6).

The microphone array 305 is used to detect the user's speech, or to record audio information about the user's environment. The microphone array 305 may include audio filters to localize a user's speech from background audio noise. The microphone array 305 may be used to detect verbal commands of the user, which may be used to control the AR, VR and/or MR environment produced by the neckband 300 and/or an AR, VR and/or MR environment produced by a coupled device, such as the eyewear device shown in FIGS. 1-2 and 4-7. The user's verbal commands may also be used to control a coupled device such as a mobile device, tablet or laptop.

In examples in which the neckband 300 operates without an eyewear device (such as the eyewear device shown in FIGS. 1-2 and 4-7), the neckband 300 may also include a speaker or other audio system (not shown) capable of playing back audio content to a user. This may be wireless headphones communicatively coupled to the neckband 300, wired or wireless earbuds connected to the neckband 300, or any other standard form of audio output. The microphone array 305 and audio system may provide the user with an audio-based AR, MR and/or VR experience.

The microphone array 305 may be symmetrically located at two points on the neckband 300, such as in the multifunction modules of multifunction compartment 330a and multifunction compartment 330b of the first arm 140 and second arm 145, respectively. The microphone array 350 may also be located at more than two points on the neckband 300. The microphone array 350 conveys audio information to the processor embedded in the computation compartment 130, and/or a processor in a coupled mobile device, such as the mobile device as described in FIG. 6. The microphone array and audio functionality may operate independently of the multifunction compartments 330a and 330b, and may thus provide an "always-on" audio assistance during operation of the neckband 300.

The projector 325 is used to project visual information from the neckband 300 onto a surface visible to the user. The projector 325 may be a pico projector, or any other source of visual information capable of being projected onto a user's environment and viewable to the user. Examples of visual information may include photographs, videos, generated 3D objects, etc. In some examples, the surface may be the screen of a coupled device, such as the mobile device as described in FIG. 6. In some examples, the surface may be a surface in the user's environment. For example, the projector may project a keyboard for the user to type on, while the reference camera 320 and/or other detectors determine the user's input to the keyboard. In another example, the projector 325 may project an AR, VR and/or MR environment onto the screen of a device in communication with the neckband 300. In another example, the projector 325 may project video onto a surface or the screen of a device in communication with the neckband 300. As shown in FIG. 3, the projector 325 is located on the neckband 300 in the multifunction module of multifunction compartment 330b on the second arm 145. The projector 325 is located at the end of the arm 145 and projects in the same direction as the user's gaze. The projector 325 may be located at the end of the first arm 140 or the second arm 145 in order to project visual content in the user's field of view.

In some embodiments, the neckband 300 may be sized to a user's neck. For example, the neckband 300 may be formed in different sizes, such as Small, Medium and Large. The length of the first arm 140, second arm 145, and computation compartment 130 may be different for each size of the neckband 300. For example, if the neckband 300 is in a size Small, the length of the first arm 140, second arm 145 and computation compartment 130 are smaller than the length of the first arm 140, second arm 145 and computation compartment 130 if the neckband 300 is in a size Large. In some embodiments, the neckband 300 may be deconstructed into three sub-assemblies: the first arm 140, the second arm 145, and the computation compartment 130. The first arm 140 may be removable from the computation compartment 130 at the neckband junction 335a. The second arm 145 may be removable from the computation compartment 130 at neckband junction 335b. The first arm 140 may be removed if the user wishes to swap in a different battery or a different set of multifunction modules in the multifunction compartment 330a of first arm 140. Likewise the second arm 145 may be removed if the user wishes to swap in a different battery or a different set of multifunction modules in the multifunction compartment 330b of the second arm 145. The computation compartment 130 may be replaced with a new computation compartment 130 if the user wishes to upgrade the processing power of neckband 300, while retaining the first arm 140 and second arm 145. Each of the sub-assemblies of the first arm 140, second arm 145 and computation compartment 130 may be a different color or otherwise aesthetically customizable to the user's preferences, and may be changed as the user desires. The sub-assemblies may also be swapped out to replace batteries, increase or reduce the weight of the neckband 300, change the size of the neckband 300, or otherwise increase the user's comfort level wearing the neckband 300. The sub-assemblies allow neckband 300 to be adaptable to a user's preferences without necessitating full replacement of the neckband 300. Instead, sub-assemblies may be swapped out and replaced individually.

The neckband junctions 335a and 335b may be magnetically coupled, such that the first arm 140 and second arm 145 are removable from the computation compartment 130. Information from the computation compartment 130 may pass through the neckband junction 335b to the second arm 145 and through the neckband junction 335a to the first arm 140 through magnetic induction, fiber-optics, or any another form of data transfer. The neckband junctions 335a and 335b may also be hinged junctions, such that the first arm 140 and second arm 145 may fold or bend at junctions 335a and 335b, allowing the neckband 300 to be reduced to a smaller form factor when the neckband 300 is not on the user neck, such as for storage or transport of the neckband 300. In some examples, neckband junctions 335a and 335b may be flexible, allowing the first arm 140 and second arm 145 to be adjusted relative to the computation compartment 130 to better conform to a user's neck. The first arm may be flexed from the neckband junction 335a in the x and/or z directions. The second arm may be flexed from the neckband junction 335b in the x and/or z directions.

The battery in the battery compartment 125 of the first arm 140 may be the same battery in the battery compartment 125 of the second arm 145. This allows for even weight and heat distribution across the neckband 300, improving the user's temperature comfort level as well as ensuring that the weight is evenly distributed across the user's shoulders.

Figure 4:
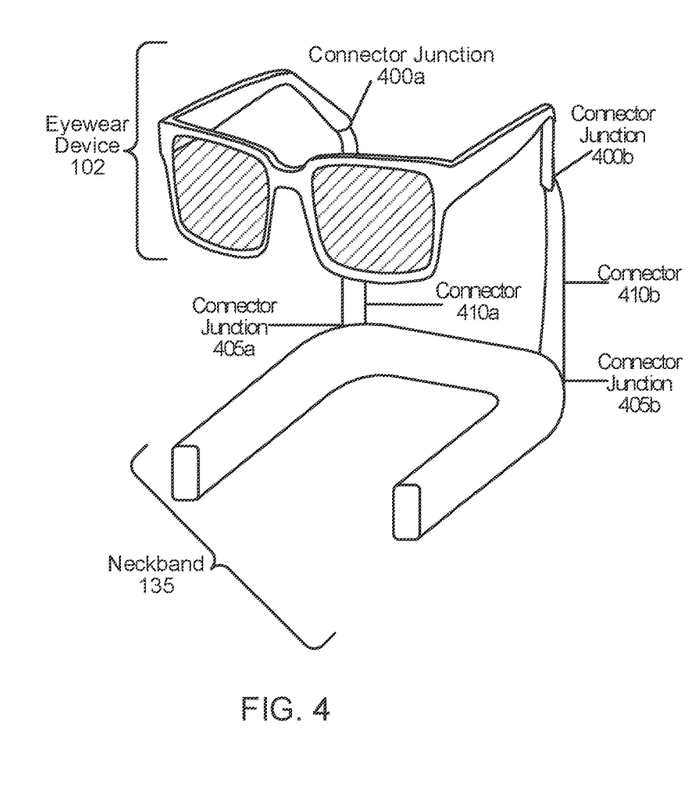
FIG. 4 is a diagram of connecting architecture in a distributed system, in accordance with an embodiment.
Figure 5:
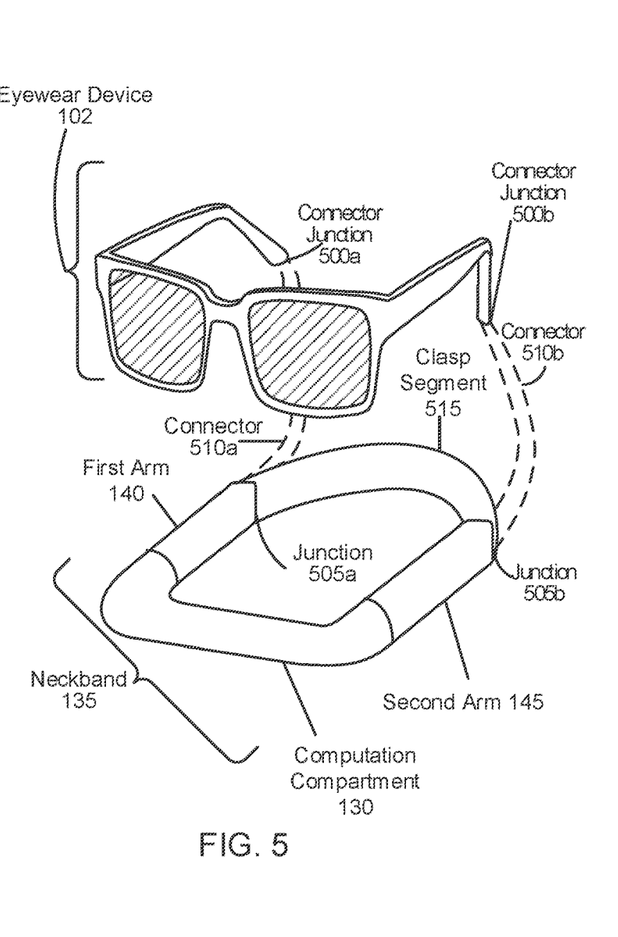
FIG. 5 is a diagram of another connecting architecture in a distributed system, in accordance with an embodiment.
Figure 6:
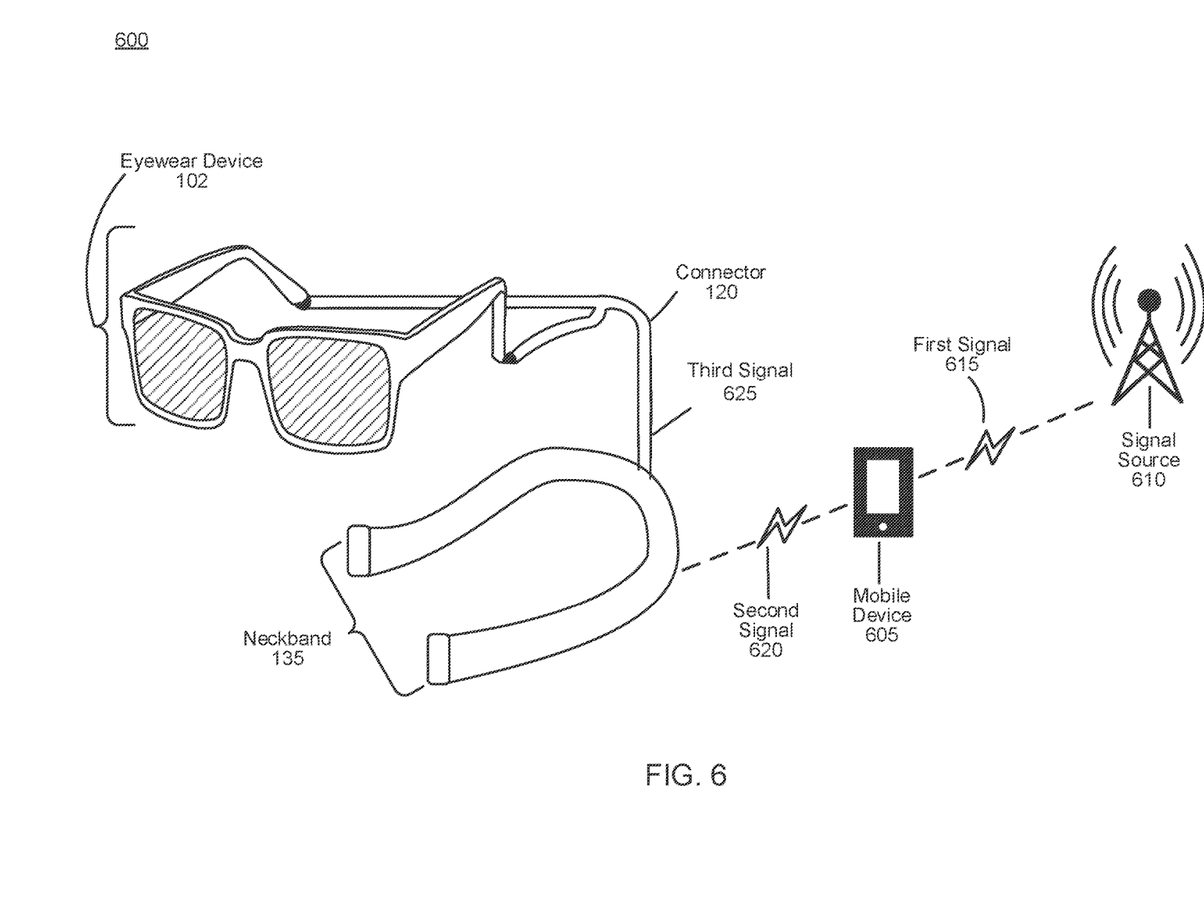
FIG. 6 is a diagram of a signal pathway, in accordance with an embodiment.

The additional features available from the units in the multifunction compartments 330a and 330b supplement the AR, VR and/or MR experience provided by a coupled AR, VR and/or MR eyewear device or other coupled device, such as the eyewear device 102 as shown in FIGS. 1-2 and 4-7. The units in the multifunction compartments 330a and 330b may also allow the neckband 300 to be a solo AR, VR and/or MR device, or an AR, VR and/or MR device used in conjunction with a coupled mobile device, such as the mobile device as shown in FIG. 6.

FIG. 4 is a diagram of connecting architecture in a distributed system 100, in accordance with an embodiment. The neckband 135 is attached to the eyewear device 102 by the connectors 410a and 410b. Connector 410a is attached to the end tip of the eyewear device 102 at connector junction 400a and to the neckband 135 at the connector junction 405a. Connector 410b is attached to the end tip of the eyewear device 102 at connector junction 400b and to the neckband 135 at the connector junction 405b. Neckband 135 may be the neckband 300 as shown in FIG. 3. Connectors 410a and 410b provide power from the neckband 135 to the eyewear device 102. Connectors 410a and 410b convey information between the eyewear device 102 and the neckband 135.

As shown in FIG. 4, the neckband device 135 may be wirelessly coupled to the eyewear device 102. In this example, connectors 410a and 410b may convey power from the neckband 135 to the eyewear device 102.

The connector architecture shown in FIG. 4 may allow for further stabilization of the neckband 135 on a user's neck, as the neckband 135 is secured to the eyewear device 102 at two points, connector junction 405a and connector junction 405b, along the length of the neckband 135. The connector architecture shown in FIG. 4 allows the eyewear device 102 to be worn around a user's neck when the eyewear device 102 is not on a user's head. Thus the connectors 410a and 410b allow the eyewear device 102 to be anchored to the stable neckband 135 as the eyewear device 102 may rest on a user's chest or breastbone.

FIG. 5 is a diagram of another connecting architecture in a distributed system 100, in accordance with an embodiment. The neckband 135 is worn around a user's neck like a necklace, such that the computation compartment 130 is in front of the user's neck, resting near the user's breastbone, while the first arm 140 and second arm 145 are located at either side of the user's neck. The first arm 140 and second arm 145 are connected by a clasp segment 515, which may be removable from the neckband 135 at junctions 505a and/or 505b. Junctions 505a and 505b may be hinges, such that the neckband 135 can be put on or taken off of a user's neck by opening and closing the hinges at junctions 505a and/or 505b. The clasp segment 515 may be padded and flexible. The clasp segment 515 may be a padded band. Thus the clasp segment 515 provides a comfortable and removable anchor from which the neckband 135 may be hung around a user's neck.

As shown in FIG. 5, connectors 510a and 510b may be optionally connected to the neckband 135 and clasp segment 515 assembly. In some embodiments in which the neckband 135 is in wireless communication with the eyewear device 102, connectors 510a and 510b may be removed entirely from the neckband 135 and clasp segment 515 assembly. In some embodiments in which the neckband 135 is in wireless communication with the eyewear device 102, the connectors 510a and 510b may be present, but may serve only to transmit power from the neckband 135 to the eyewear device 102. In these embodiments, the connectors 510a and 510b may be very thin, as only power need be conveyed through the wires of connectors 510a and 510b. In some embodiments in which the neckband device 135 is not in wireless communication with the eyewear device 102, the connectors 510a and 510b convey both power and information between the neckband 135 and eyewear device 102. Connector 510a is attached to the end tip of the eyewear device 102 at connector junction 500a. Connector 510a is attached to the neckband 135 at connector junction 505a. Connector 510b is attached to the end tip of the eyewear device 102 at connector junction 500b. Connector 510b is attached to the neckband at connector junction 505b.

The connecting architecture shown in FIG. 5 allows the neckband 135 to be secured around a user's neck, with our without physical connectors to an eyewear device 102. In embodiments in which the communication between the neckband 135 and the eyewear device 102 is wireless, connecting architecture shown in FIG. 5 may be employed.

FIG. 6 is a diagram of a signal pathway 600, in accordance with an embodiment. In signal pathway 600, a signal source 610 sends a first signal 615 to a mobile device 605. The mobile device sends a second signal 620 to the neckband 135. The connector 120 communicates a third signal 625 to the eyewear device 102. This signal pathway may be reversed, such that the eyewear device 102 sends a third signal 625 to the neckband 135 through the connector 120, the neckband 135 sends a second signal 620 to the mobile device 605, and the mobile device sends a first signal 615 to the signal source 610.

The signal source 610 is a cellular network, capable of linking the mobile device 605 to the internet via the cellular network of signal source 610. The signal source may also be from any combination of local area and/or wide area networks, using both wired and/or wireless communication systems. The signal source 610 may use standard communication technologies and/or protocols to send first signal 615. Signal 615 may be sent using technologies such as Ethernet, 802.11, worldwide interoperability for microwave access (WiMAX), 3G, 4G, 5G, code division multiple access (CDMA) digital subscriber line (DSL), etc. In some examples, the mobile device may be any device having computer functionality, such as a personal digital assistant (PDA), a smartphone, a laptop, tablet, or another suitable device. In some examples, the mobile device may be a watch, bracelet, or any other wearable device that may track a user's hand motions. Mobile device 605 is configured to communicate with both the signal source 610 and the neckband 135. In some embodiments, the neckband 135 communicates directly with the signal source 610, such that the first signal 615 sent from the signal source 610 is sent directly to the neckband 135.

The mobile device 605 communicates the second signal 620 to the neckband 135. The second signal 620 may be a wired or wireless signal. The mobile device 605 may have an application used to control the AR, VR, and/or MR environment produced by the neckband 135 and/or eyewear device 102. The application may be run on any mobile device operating system, such as an iOS operating system, an Android operating system, etc. The application on the mobile device 605 may control other features on the neckband 135 and eyewear device 102, such as turning ON or OFF a voice command feature, adjusting volume, brightness, etc. The application on the mobile device 605 may allow for personalized settings of the neckband 135 and eyewear device 102.

The mobile device 605 may serve as an additional processor to the processor located in the computation compartment of neckband 135. The mobile device may process information from the glasses 102 and/or the neckband 135. The mobile device 605 may have wired or wireless communication with neckband 135, depending on if there are latency issues with the receipt or transmittal of processing information. In some examples, the mobile device 605 may serve as a battery backup for the battery compartments located on the neckband 135. In some examples, the neckband 135 receives information about sensors on the eyewear device 102 from the mobile device 605.

The second signal 620 may be a wireless signal, such as a Bluetooth signal, Wi-Fi signal, or any other suitable wireless signal. In some examples, the second signal 620 may be an electric, magnetic or optic signal conveyed through a wire, or any other non-wireless signal. The second signal 620 may thus be information from the neckband 135 conveyed to the mobile device 605, or information from the mobile device 605 to the neckband 135. This information may be processed by the mobile device 605.

The mobile device 605 is thus coupled to the neckband 135 by at least the second signal 620. A projector on the neckband 135 may project an image, video, or any visual content onto the screen of the mobile device 605. The mobile device 605 may thus serve as an additional AR, VR and/or MR device, onto which an AR, VR and/or MR environment can be projected from the neckband 135. The mobile device 605 may operate with the neckband 135 only, such that the eyewear device 102 is not included in the user's AR, VR and/or MR experience and the AR, VR and/or MR environment is entirely generated by the neckband 135 and mobile device 605.

The mobile device 605 may include a camera (not shown) with the ability to track the hand, body and/or facial movements of a user. The mobile device 605 may have an Artificial Intelligence (AI) or Machine Learning (ML) interface, which may learn a user's hand, body and/or facial movements to anticipate and predict a user's command or intention. In some examples, the camera on the mobile device 605 may have a 3D user capture feature, allowing the user's body to be 3-dimensionally rendered and tracked. The camera on the mobile device may provide a 3D depth map of a user's face. The camera may be a passive camera or active camera including a depth camera assembly, capable of scanning a room or otherwise mapping a user's environment. The camera assembly may be a TOF system, SL system, mono or stereo vision (passive and/or active), or any other system capable of producing a depth map. The camera assembly may provide a fully 3D description of the user's environment, such as a room in which a user is standing in or other physical structures around the user. The camera on the mobile device 605 may provide 3D information to the neckband 135 and/or eyewear device 102.

The mobile device 605 may also have an audio and/or visual streaming feature, allowing the user to perceive audio/visual information that may supplement the AR, VR and/or MR environment produced by the neckband 135 and/or eyewear device 102. The mobile device 605 may include a haptic feature, wherein the user's physical interaction with the mobile device 605 is translated as a command to the neckband 135 and/or eyewear device 102.

The mobile device 605 may be separated into sub-assemblies. For example, one half of the mobile device 605 may be held in a user's right hand, while the second half of the mobile device 605 may be held in a user's left hand. Thus the user could independently transmit commands from each hand to the neckband 135 and/or the eyewear device 102. If the mobile device 605 is a watch or other wearable device, the mobile device 605 may track a user's hand motions. Tracked hand motions may be converted into commands and relayed to the neckband 135 and/or the eyewear device 102.

The mobile device 605 may thus supplement the AR, VR and/or MR environment provided by the eyewear device 102 and/or neckband 135.

Figure 7:
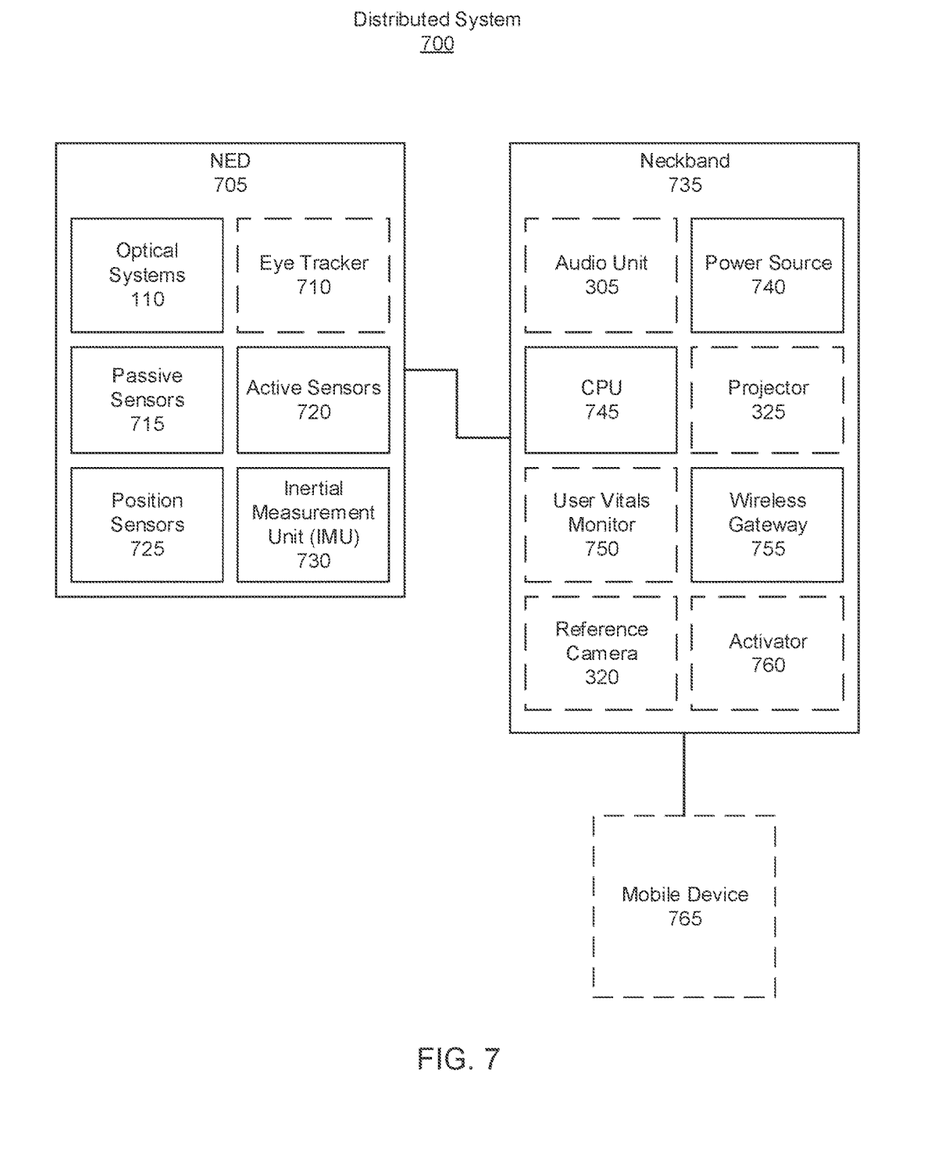
FIG. 7 is a block diagram of a distributed system, near-eye-display and mobile device system, in accordance with an embodiment.

FIG. 7 is a block diagram of a distributed system 700, in accordance with an embodiment. Distributed system 700 includes an eyewear device 705, a neckband 735, and a mobile device 765. The neckband 735 is connected to both the eyewear device 705 and the mobile device 765. The neckband 735 may be the neckband 135 as described in FIGS. 1-2 and 4-6. The neckband 735 may be the neckband 300 as described in FIG. 3. The eyewear device 705 may be the near eye display 100 as shown in FIG. 1-6. The mobile device 765 may be the mobile device 605 as shown in FIG. 6. In alternative configurations of system 700, different and/or additional components may be included. The system 700 may operate in a VR system environment, an AR system environment, an MR system environment, or some combination thereof.

The eyewear device 705 includes optical systems 110, as described with reference to FIG. 1. The eyewear device 705 may also include an eye tracker 710, one or more passive sensors 715, one or more active sensors 720, one or more position sensors 725, and an Inertial Measurement Unit (IMU) 730. As shown in FIG. 7, the eye tracker 710 may be an optional feature of the eyewear device 705.

The eye tracker 710 tracks a user's eye movement. The eye tracker 710 may include at least a dichroic mirror, for reflecting light from an eye area towards a first position, and a camera at the position at which the light is reflected for capturing images. Based on the detected eye movement, the eye tracker 710 may communicate with the neckband 735, CPU 745 and/or mobile device 765 for further processing. Eye tracking information collected by the eye tracker 710 and processed by the CPU 745 of the neckband 735 and/or mobile device 765 may be used for a variety of display and interaction applications. The various applications include, but are not limited to, providing user interfaces (e.g., gaze-based selection), attention estimation (e.g., for user safety), gaze-contingent display modes (e.g., foveated rendering, varifocal optics, adaptive optical distortion correction, synthetic depth of field rendering), metric scaling for depth and parallax correction, etc. In some embodiments, a processor in the mobile device 765 may also provide computation for the eye tracker 710.

Passive sensors 715 may be cameras. Passive sensors may also be locators, which are objects located in specific positions on the eyewear device 705 relative to one another and relative to a specific reference point on the eyewear device 705. A locator may be a corner cube reflector, a reflective marker, a type of light source that contrasts with an environment in which the eyewear device 705 operates, or some combination thereof. In embodiments in which the locators are active sensors 720 (i.e., an LED or other type of light emitting device), the locators may emit light in the visible band (~370 nm to 750 nm), in the infrared (IR) band (~750 nm to 1700 nm), in the ultraviolet band (300 nm to 380 nm), some other portion of the electromagnetic spectrum, or some combination thereof.

Based on the one or more measurement signals from the one or more position sensors 725, the IMU 730 generates IMU tracking data indicating an estimated position of the eyewear device 705 relative to an initial position of the eyewear device 705. For example, the position sensors 725 include multiple accelerometers to measure translational motion (forward/back, up/down, left/right) and multiple gyroscopes to measure rotational motion (e.g., pitch, yaw, and roll). In some embodiments, the IMU 730 rapidly samples the measurement signals and calculates the estimated position of the eyewear device 705 from the sampled data. For example, the IMU 730 integrates the measurement signals received from the accelerometers over time to estimate a velocity vector and integrates the velocity vector over time to determine an estimated position of a reference point of the eyewear device 705. Alternatively, the IMU 730 provides the sampled measurement signals to the neckband 735 and/or the mobile device 765 to process the computation required to estimate the velocity vector and the estimated position of the eyewear device 705.

The IMU 730 may receive one or more calibration parameters from the neckband 735 and/or the mobile device 765. The one or more calibration parameters are used to maintain tracking of the eyewear device 705. Based on a received calibration parameter, the IMU 730 may adjust one or more IMU parameters (e.g., sample rate). The adjustment may be determined by the CPU 745 of the neckband 735, or a processor of the mobile device 765. In some embodiments, certain calibration parameters cause the IMU 730 to update an initial position of the reference point so it corresponds to a next calibrated position of the reference point. Updating the initial position of the reference point at the next calibrated position of the reference point helps reduce accumulated error associated with the determined estimated position of the eyewear device 705. The accumulated error, also referred to as drift error, causes the estimated position of the reference point to "drift" away from the actual position of the reference point over time. In some examples, the IMU 730 is located in the neckband 735 or an IMU is present in both the neckband 735 and eyewear device 705. In some examples, the IMU 730 receives position information from both position sensors 725 on the eyewear device 705 and position sensors 725 on the neckband (not shown).

The neckband 735 includes an audio unit 305, a power source 740, a CPU 745, a projector 325, user vitals monitor 750, a wireless gateway 755, reference camera 320 and activator 760. As shown in FIG. 7, the audio unit 305, projector 325, user vitals monitor 750, reference camera 320 and/or activator 760 may be optional components on the neckband 735. In some embodiments, the neckband 735 includes one or more multifunctional compartments that interface with various functional units. The functional units can include, e.g., the audio unit 305, an additional power source, an additional processing unit (e.g., CPU), the projector 325, the user vitals monitor 750, the wireless gateway 755, the reference camera 320, and the activator 760.

The audio unit 305 may include a microphone array, as shown in FIG. 3, which may be located on the neckband 735 in close proximity to a user's mouth. The microphone array may be used to record a user's voice or detect user's voice commands. The input of the microphone array may affect the eyewear device 705. For example, in response to an ON voice command detected by the microphone array, the optical element 110, eye tracker 710, light source 715, locators 720, position sensors 725 and IMU 730 may be powered on. The audio unit 305 may also include a speaker, or any other audio input or output.

The power source 740 provides power to the optical systems 110, eye tracker 710, passive sensors 715, active sensors 720, position sensors 725 and IMU 730. The power source 740 may be the battery compartment 125 as shown in FIG. 1 and FIG. 3. Power source 740 may be a rechargeable battery, which may be recharged by the mobile device 765. The power source 740 may be turned ON or OFF in response to a voice command detected by the audio unit 305, an input of the activator 760, and/or a command received by the mobile device 765.

The CPU 745 may be any standard processor, and may be the processor embedded in the computation compartment 130 as shown in FIG. 1-3 and FIG. 5. The CPU 745 may provide all computational processing for the eyewear device 705, including the computation associated with the eye tracker 710, passive sensors 715, active sensors 720, and IMU 730. The CPU 745 may carry out calculations in parallel with the processor of the mobile device 765. A processor in the mobile device 765 may provide calculation results to the CPU 745.

The projector 325 may be located on the neckband 735 to project visual information to a user. The projector 325 may project visual information onto a surface in the user's field of view, or onto a coupled device with a screen, such as the mobile device 765.

The user vitals monitor 750 monitors vital signs and other user health indicators. Vital signs may be heart rate, pulse, estimated calorie consumption, number of steps taken by the user, the user's temperature, respiration rate, blood pressure, etc. The user vitals monitor 750 may be located in close proximity to a user's neck on the neckband 735, so that the vital signs may be accurate. For example, a pulse detection is more accurate if the vitals monitor is pressed firmly against the user's neck. The user vitals monitor 750 may be thermally isolated from the power source 740 and CPU 745 to ensure that temperature estimates are a result of the user's temperature and are unaffected by heat generated by the power source 740 and CPU 745. The user vitals monitor may be in communication with the position sensors 725 and IMU 730 to detect user steps and user movement to estimate the number of steps taken and/or calorie consumption.

The wireless gateway 755 provides signal communication with the mobile device 765 and/or the eyewear device 705. The wireless gateway 755 may convey the second signal 620 from the mobile device 605 to the neckband 135, as shown in FIG. 6. The wireless gateway 755 may be any standard wireless signal gateway, such as a Bluetooth gateway, Wi-Fi gateway, etc.

The reference camera 320 provides visual information about a user's activity to the CPU 745, mobile device 765, and/or the eyewear device 705. For example, the reference camera 320 may provide an image of a user pointing at an object, in response to which the neckband 735 and eyewear device 705 may provide further information about the indicated object. The reference camera 320 may also be used to localize IMU determinations by providing reference information about a user's position in his or her environment.

The activator 760 controls functions on the neckband 735, the eyewear device 705, and/or the mobile device 765. The activator 760 may be the activation button 315 as shown in FIG. 3. The activator 760 may power ON or OFF any of the units in the eyewear device 705 and/or neckband 735.

Distributed system 700 produces an AR, VR or MR environment to a user, or any combination thereof. The distributed system 700 is able to distribute processing, power and heat generating functions across the eyewear device 705, neckband 735 and mobile device 765. This allows each of the eyewear device 705 and neckband 735 to be adjusted to the desired weight and temperature for user comfort, as well as providing varied virtual environment interfaces and functions for the user to interact with at any of the eyewear device 705, neckband 735 and/or mobile device 765.

Additional Configuration Information

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A neckband device comprising:
a first arm and a second arm coupled together to form a shape such that the neckband device conforms to a neck of a user; and
a plurality of compartments within the neckband device, the plurality of compartments including a battery compartment for a battery that is configured to power an eyewear device and a computation compartment configured to hold a processor that is configured to compute at least one value from a sensor of the eyewear device, and the first arm includes at least one of the plurality of compartments,
wherein the neckband device is communicatively coupled with the eyewear device.

2. The neckband device of claim 1, wherein the first arm and the second arm are coupled to, and removable from, the computation compartment.

3. The neckband device of claim 1, wherein at least one of the first arm, the second arm and the computation compartment contains a multifunction compartment, of the plurality of compartments, and the multifunction compartment interfaces with a functional unit, the functional unit comprising at least one of:
a memory unit;
a processing unit;
a microphone array;
a projector; and
a camera.

4. The neckband device of claim 3, wherein the functional unit is part of the second arm and the functional unit comprises the camera.

5. The neckband device of claim 3, wherein the functional unit is part of the second arm, the functional unit comprising the projector, and the projector is configured to project visual content onto a surface.

6. The neckband device of claim 1, further comprising a microphone array, the microphone array configured to record the user's voice and provide audio data to a processor.

7. The neckband device of claim 1, further comprising:
a wireless gateway, the wireless gateway configured to communicatively couple the neckband device with the eyewear device.

8. The neckband device of claim 1, further comprising:
a wireless gateway, the wireless gateway configured to communicatively couple the neckband device with at least a mobile device.

9. The neckband device of claim 1, further comprising a connector having:
a first connector arm latched near a first end tip of the eyewear device;
a second connector arm latched near a second end tip of the eyewear device; and
a third connector arm latched to the neckband device, and the third connector arm is coupled to the first connector arm and the second connector arm.

10. The neckband device of claim 9, the connector further comprising:
an adjustable tension slider configured to secure the eyewear device to the user's head by compressing the first connector arm to the second connector arm, and wherein the connector provides power and information from the neckband device to the eyewear device.

11. The neckband device of claim 1, further comprising:
a vitals sensor configured to determine a vital sign of the user.

12. The neckband device of claim 1, further comprising:
an IMU sensor configured to determine a position of the neckband device relative to an environment of the user.

13. The neckband device of claim 1, wherein a first end of the first arm and a first end of the second arm are coupled together using a clasping segment, and a second end of the first arm and a second end of the second arm are coupled together with the computation compartment.

14. A system comprising:
an eyewear device that includes a sensor;
a neckband device comprising:
a first arm and a second arm coupled together to form a shape such that the neckband device conforms to a neck of a user, and
a plurality of compartments within the neckband device, the plurality of compartments including a battery compartment for a battery that is configured to power the eyewear device and a computation compartment configured to hold a processor that is configured to compute at least one value from the sensor, and the first arm includes at least one of the plurality of compartments,
wherein the neckband device is communicatively coupled with the eyewear device.

15. The system of claim 14, wherein at least one of the first arm, the second arm and the computation compartment contains a multifunction compartment, of the plurality of compartments, and the multifunction compartment interfaces with a functional unit, the functional unit comprising at least one of:
a memory unit;
a processing unit;
a microphone array;
a projector; and
a camera.

16. The system of claim 15, wherein the functional unit is part of the second arm and the functional unit comprises the projector, and the projector is configured to project visual content onto a surface.

17. The system of claim 14, further comprising:
a wireless gateway, the wireless gateway configured to communicatively couple the neckband device with at least a secondary user device,
wherein the secondary user device is selected from a group consisting of a smartphone, a laptop, a tablet, a personal digital assistant, a watch, and a bracelet.

18. The system of claim 17, wherein the secondary device functions as an additional processor for the neckband device.

19. The system of claim 17, wherein the secondary device includes a camera assembly that determines a three dimensional (3D) description of an environment of the user, and the secondary device provides the 3D description to at least one of the neckband and eyewear device.

20. The system of claim 17, wherein the secondary device includes a camera assembly that determines a three dimensional description of a face of the user, and the secondary device provides the 3D description to at least one of the neckband and eyewear device.

* * * * *